United States Patent [19]

Chiesi et al.

[11] Patent Number: 5,351,683
[45] Date of Patent: Oct. 4, 1994

[54] DEVICE FOR THE ADMINISTRATION OF POWDERED MEDICINAL SUBSTANCES

[75] Inventors: Paolo Chiesi; Paolo Ventura; Isabella Panza, all of Parma, Italy

[73] Assignee: Chiesi Farmaceutici S.p.A., Parma, Italy

[21] Appl. No.: 11,785

[22] Filed: Feb. 1, 1993

Related U.S. Application Data

[63] Continuation of Ser. No. 682,561, Apr. 9, 1991, abandoned.

[30] Foreign Application Priority Data

Apr. 12, 1990 [IT] Italy .............................. 20025 A/90

[51] Int. Cl.$^5$ ............................................ A61M 15/00
[52] U.S. Cl. ........................... 128/203.12; 128/203.15
[58] Field of Search ..................... 128/203.12, 203.15, 128/203.21, 203.23, 203.24

[56] References Cited

U.S. PATENT DOCUMENTS

| | | | |
|---|---|---|---|
| 2,259,759 | 10/1941 | Lufkin | 128/203.23 |
| 2,310,681 | 2/1943 | Derham et al. | 128/203.23 |
| 2,609,817 | 9/1952 | Falcone | 128/203.23 |
| 4,069,819 | 1/1978 | Valentini et al. | 128/203.15 |
| 4,274,403 | 6/1981 | Struve | 128/203.15 |
| 4,889,114 | 12/1989 | Kladders | 128/203.15 |

FOREIGN PATENT DOCUMENTS 2041763 9/1980 United Kingdom .......... 128/203.15

Primary Examiner—Edgar S. Burr
Assistant Examiner—Stephen R. Funk
Attorney, Agent, or Firm—Oblon, Spivak, McClelland, Maier & Neustadt

[57] ABSTRACT

An inhaler for the local administration of powdered drugs to the respiratory tract. The inhaler includes a nozzle and a main body which itself defines a storage chamber for the medicinal substance, a dosing mechanism which supplies precisely measured doses of the drug and a dispensing system which pours the dose of the drug delivered into a collecting chamber. A cavity of the nozzle communicates with the collecting chamber through a central channel designed to reduce air flow resistance as much as possible. Lateral holes provided in the body of the inhaler allow for the passage of air from the outside. Upon inhalation, a negative pressure is created in the chamber in which the dose of powder delivered is collected, drawing an air inflow from the outside. The air flow is mixed with the medicinal substance particles and through the central channel, enters the cavity of the nozzle from where it is directly inhaled.

4 Claims, 3 Drawing Sheets

DEVICE FOR THE ADMINISTRATION OF POWDERED MEDICINAL SUBSTANCES

This application is a continuation of copending application Ser. No. 07/682,561, filed Apr. 9, 1991, now abandoned.

BACKGROUND OF THE INVENTION

1. Field of the Invention

This invention relates to an apparatus for the inhalation of powders to be used for the direct administration of drugs to the respiratory tract.

2. Description of the Related Art

The administration of drugs by inhalation plays an important role in the treatment of respiratory disorders.

The action of the drug is in fact more rapid and, moreover, prolonged by this route. Local administration to the target organ also means that it is possible to use much smaller quantities of the active principle, with less frequent side effects.

The delivery systems available for local administration of drugs to airways are nebulizers, metered dose inhalers and powder inhalers.

Nebulizers provide effective treatment, but as a result of their dimensions they are restricted to domestic use.

Metered dose inhalers are of small dimensions and are easily portable, but the correct use thereof requires perfect coordination of inhalation and of aerosol release, and thus many patients have difficulties in employing them properly.

The dry powder inhalers constitute a valid alternative for the administration of drugs to the airways.

The essential advantage of powder inhalers is that they do not require coordination of movements, as release of the active principle is operated by the patient's inhalation.

One common feature of powder inhalers is that they are activated by a turbulent air flow generated by inhalation by the patient.

This air flow created in the interior of the inhaler carries out the drug, contained in appropriate dosage units or chambers in the form of micronized powder.

Devices for the inhalation of powders can be divided into two basic types according to the dispensing and delivery means for the active principle:

I. Single dose inhalers for the administration of subdivided doses of the active compound enclosed in hard gelatine capsules.

II. Multidose inhalers preloaded with quantities of active principle sufficient for complete treatment cycles, each single dose being distributed in a practical and rapid manner at the time of use, according to the dosage program, allowing, where required, for the administration of two doses simultaneously.

The delivery apparatus is disposable at the end of the treatment cycle.

As a result of their relatively complicated structural mechanisms, the inhalers of type I (examples of which are described in EP 41783 (Fisons), BE 813143 (ISF), GB 2064334 and BE 886531 (Glaxo), EP 147755 (Boehringer) and EP 271029 (Mect) are relatively difficult for patients with poor manual dexterity.

Moreover, in view of the fact that the dose of the drug to be inhaled is enclosed in a capsule of gelatine, they present some significant disadvantages:

the inhalers have to be charged with the unit dose before each use and each time the operation is completed they must be empty and clean from any capsule and powder residue;

the capsule is often not split correctly on the first attempt and the patient has to perform several operations;

the capsule is often not emptied completely, and the dose delivered is not constant.

An apparatus of type II, which, has proven to be advantageous for the administration of powdered medicinal substances, is described in the Applicant's British Patent No. 2041763.

The apparatus consists essentially of the following elements:

a nozzle which is free to rotate on a main body;

a storage chamber for the medicinal substance, of such a volume that it contains a sufficient quantity of the drug for a complete treatment cycle;

a dosing means which, during each rotation through 180°, delivers one dose of the medicinal substance;

a dispensing system which, during the rotation, pours the dose into a collecting chamber in communication towards its top with the cavity of the nozzle and towards its bottom with a ventilation chamber, itself in communication with the outside by means of two symmetrical holes.

In operation, the patient rotates the nozzle on the central body through 180°, thereby effecting distribution of the dose, then inhales via the nozzle, generating an air flow which takes up the powder and carries it out along the central cavity, from where it is inhaled directly upon the act of inhalation.

European Patent Application No. 87850060 (Aktiebolaget Draco), filed after Applicants' above-identified British patent, describes an inhaler, whose working depends substantially upon the presence of deflector devices comprising helical elements intended to ensure effective disintegration of the powder aggregates into particles suitable for inhalation and for reaching the deeper parts of the respiratory tract.

This apparatus does not in fact have any particular advantages compared to the device known beforehand.

The deflector devices do not constitute a real improvement, since the inhaler of British Patent No. 2041763 already provides for the presence in the interior of the central conduit of helically extending blades to impart a turbulent motion to the powder composition.

Moreover, the Draco inhaler is characterized by a certain structural complexity and is particularly designed for the administration of small doses of powder, less than 1 mg upon each actuation.

An inhaler of the multidose type in which the individual doses of powder are contained in each of a series of plastic blisters is described in Glaxo's EP 211595.

This case also relates to a rather complex apparatus, the operation of which may present problems for the patient and may be accompanied, as in the case of the inhalers of type I, by disadvantages, such as incorrect opening of the container holding the drug, with a consequent lack of uniformity of the dosage and loss of the active powder in the interior of the internal cavity.

The ideal inhaler, on the other hand, should allow for constant and correct administration of the drug, with minimum effort on the part of the patient.

A multidose device for the inhalation of powders of type II, if actually operational and well designed, has real advantages and is extremely suitable by virtue of its simplicity of operation (requiring no particular skill on the part of the patient), the constancy and reproducibility of the dose delivered by means of an efficient distribution system, and the absence of waste arising from the opening of a capsule or blister.

SUMMARY OF THE INVENTION

This invention relates to a new powder inhaler designed to ameliorate the metering system of the dose and to optimize the flow characteristics by reducing and redistributing the resistance to air flow, induced by the pressure drops created in the interior of the apparatus upon inhalation.

In dry powder inhalers the drug is provided as a finely milled powder which consists of drug particles in large aggregates. Most of the particles are too large to penetrate into the lungs. The energy provided by the inspiratory flow rate has to break up the aggregates into small particles before they can be carried into the lower airways. The higher the flow rate, the larger the number of respirable drug particles.

The construction of the powder device has a great effect on the redispersion of the small drug particles. Thus, the therapeutically significant lung deposition can be enhanced by optimizing the powder device.

In order to reduce the flow resistance of the air inhaled in the device of the invention, a particular study was made of the optimum dimensions of the central channel, both with respect to the width and with respect to the length in, absolute and in relation to the volume of the cavity of the nozzle.

It was in fact demonstrated that in order to obtain good flow behavior, the occurrence of pressure drops in the areas above the zone in which the powder is mixed with the air flow must be prevented as far as possible.

To attain this aim, the length and the width of the central channel and the size of the cavity of the nozzle are of fundamental importance.

The greater flow resistance is moreover to be localized in the lower part of the channel where the powder is mixed with the air flow, and more energy is required for the disaggregation of the particles.

BRIEF DESCRIPTION OF THE DRAWINGS

The invention will now be described in more detail with reference to the accompanying drawings, wherein.

DESCRIPTION OF THE PREFERRED EMBODIMENT

Figure 1:
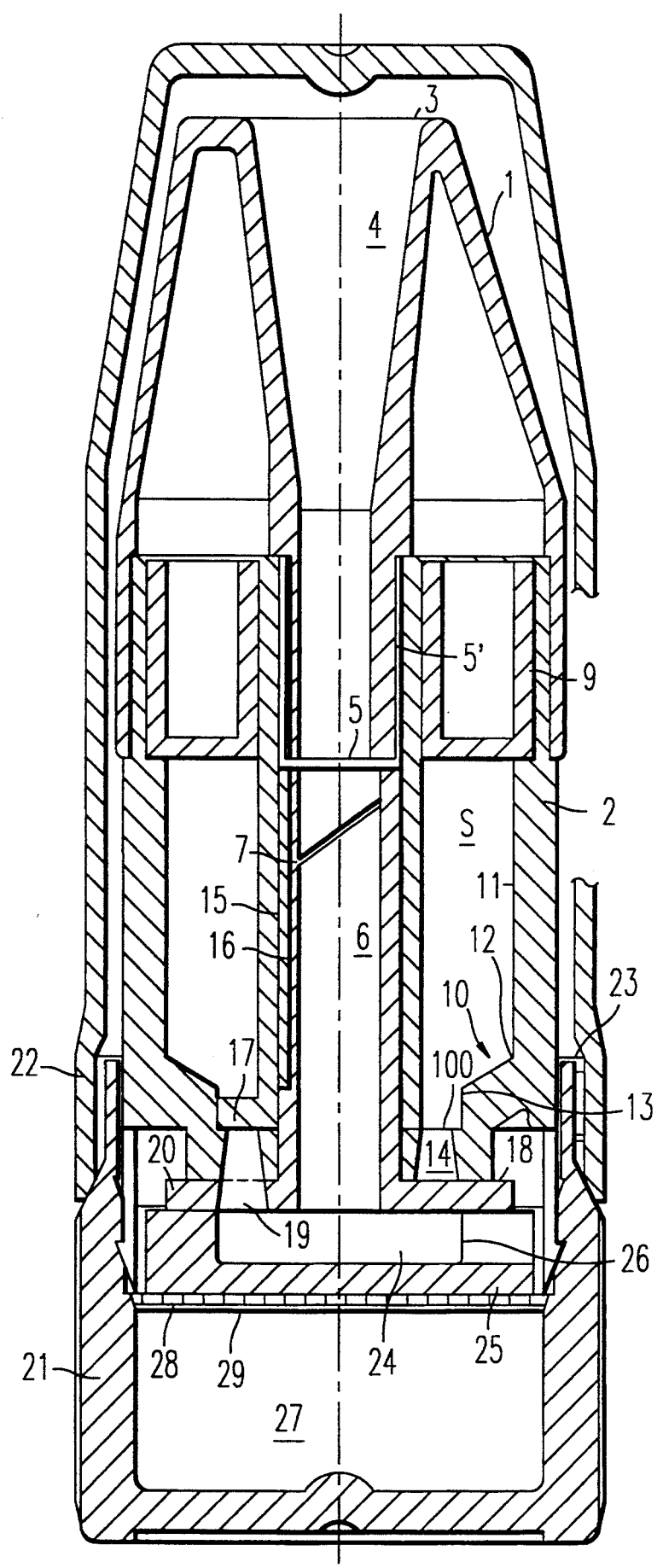
FIG. 1 shows a cross-sectional view of the inhaler of the present invention.

The inhaler, the longitudinal section of which is illustrated in FIG. 1, consists essentially of a nozzle 1, mounted on a main body, designated in general by the reference numeral 2.

The nozzle 1 has an aperture 3 communicating with an internal cavity 4 tapering towards a circular hole 5 in direct communication with a central channel 6, consisting of a tubular element 7 disposed axially relative to the body 2 and free to rotate relative to the latter with rotations through 180° alternately in one direction and in the other. This element 7 is integral with a crown 5' forming part of the nozzle 1 and defining the hole 5. The crown 5' may be similar to that shown in FIG. 2 of Applicants' British Patent 2041763. The body 2 defines a storage chamber 8 for a powdered medicinal substance, the volume of this chamber advantageously being such that it contains a sufficient quantity of the drug for a complete treatment cycle. A closure element 9 defines the upper part of the chamber 8 and is inserted under pressure between the upper internal part of the body 2 and the central tubular element 7 by means of a plurality of sealing rings.

The lower part of the chamber 8 is defined by a disc 10 connected to the wall 11 of the chamber 8 by means of an inclined surface 12 forming, together with the base or flat band surface 10a of the disc 10, a vertical annular surface 13. A dosing hole 14 is provided on one side of the disc 10, of a volume corresponding exactly to the dose of the drug to be delivered.

The outer surface of the element 7 is provided with a longitudinal groove 15, engaged by a complementary relief formed on the inner surface of a further tubular element 16.

The two elements 7 and 16 are firmly connected to one another both by the abovementioned groove system and by the presence of annular retaining reliefs on the outer surface of the element 7.

A rotating diaphragm 17 is integral with the bottom end of the tubular element 16, the diaphragm being supported on the disc 10 and cooperating with the annular surface 13, as well as being interrupted by a section of a length corresponding substantially to the length of the dosing hole 14.

A dispensing disc 18 is keyed to the end portion of the element 7, below the disc 10, the dispensing disc being provided with a dispensing hole 19 adapted to register, as will be described hereinafter, with the dosing hole 14.

The dispensing disc 18 consists of two concentric semicircular sections of slightly different diameters, defining two diametrically opposite teeth. During the rotation of the disc, these teeth engage a projection 20 provided below the body 2 to act as a stop means for the teeth.

This solution allows the dosing disc to rotate only through 180° alternately in one direction and in the other. The base of the body 2 is inserted by means of a groove system into a larger cylindrical element 21, on the outer surface of which, in the upper part thereof, is provided a thread, on to which the protective cap 22 of the inhaler is screwed. At the level of this thread, a plurality of slots 23 adapted for air intake are cut between the two cylindrical bodies 2 and 21. These aspiration slots are in communication with a ventilation chamber 24 defined at the bottom by the base 25, the upper surface of which is labyrinth-shaped as a result of the presence of curved walls 26.

The aspiration slots are essential to contribute to a negative pressure which is created in the ventilation chamber when the user inhales through the aperture of the nozzle.

The element 21 is provided with an internal chamber 27 which contains a suitable dehumidifying agent, such as silica gel, with a view to absorbing any moisture from the medicinal powder, thereby preventing the formation of agglomerates.

This chamber 27 is in communication with the chamber 8 containing the powder by means of a plurality of slots 28.

A small disc 29 of gas-permeable material is inserted between the lower surface of the base 25 and the upper surface of the chamber 27.

The metering system consists of the three elements:

the tubular element 7 disposed axially to the inhaler body and equipped at the end with a dispensing disc 18, the dispensing disc 18 being provided with a dispensing hole 19;

a further tubular element 16 equipped at the end part with a semicircular diaphragm 17;

a small plate or disc 10, with a central circular hole, constituted by the inclined surface 12 whose upper surface is greatly inclined towards the inside and of the internal horizontal and flat annular band 10a, provided with a dispensing hole 14 of a volume corresponding exactly to the dose of the drug to be delivered.

The surfaces 12 and 10a of the disc 10, are connected by the vertical annular surface 13, and form at the bottom of the disc 10 a chamber to collect the powder, whose falling inside is helped by the inclination of the surface of the peripheral annular band.

Prior to initial use, the chamber 8 is filled with a sufficient quantity of the drug for a complete treatment cycle, the diaphragm 17 closing the dosing hole 14, which is then empty.

Upon use, the user effects relative rotation of the nozzle 1 and the body 2, gripping the inhaler at the nozzle with one hand and at the base of the inhaler 21 with the other hand, so as to rotate the diaphragm 17 and the dispensing disc 18 through 180°, until further rotation is blocked by engagement of a tooth of the dispensing disc and the projection 20 provided on the base of the element 2. As a result of this first rotation, the dose is loaded into the hole 14. A second rotation through 180°, in the opposite direction to the first, results in registration of the dispensing hole 19 with the dosing hole 14, so as to discharge the dose into the ventilation chamber 24, from where it can be inhaled by means of the channel 6 and the nozzle 1.

During this second phase of rotation, the diaphragm 17 once again covers the dosing hole, returning the apparatus to its initial state.

Figure 2A:
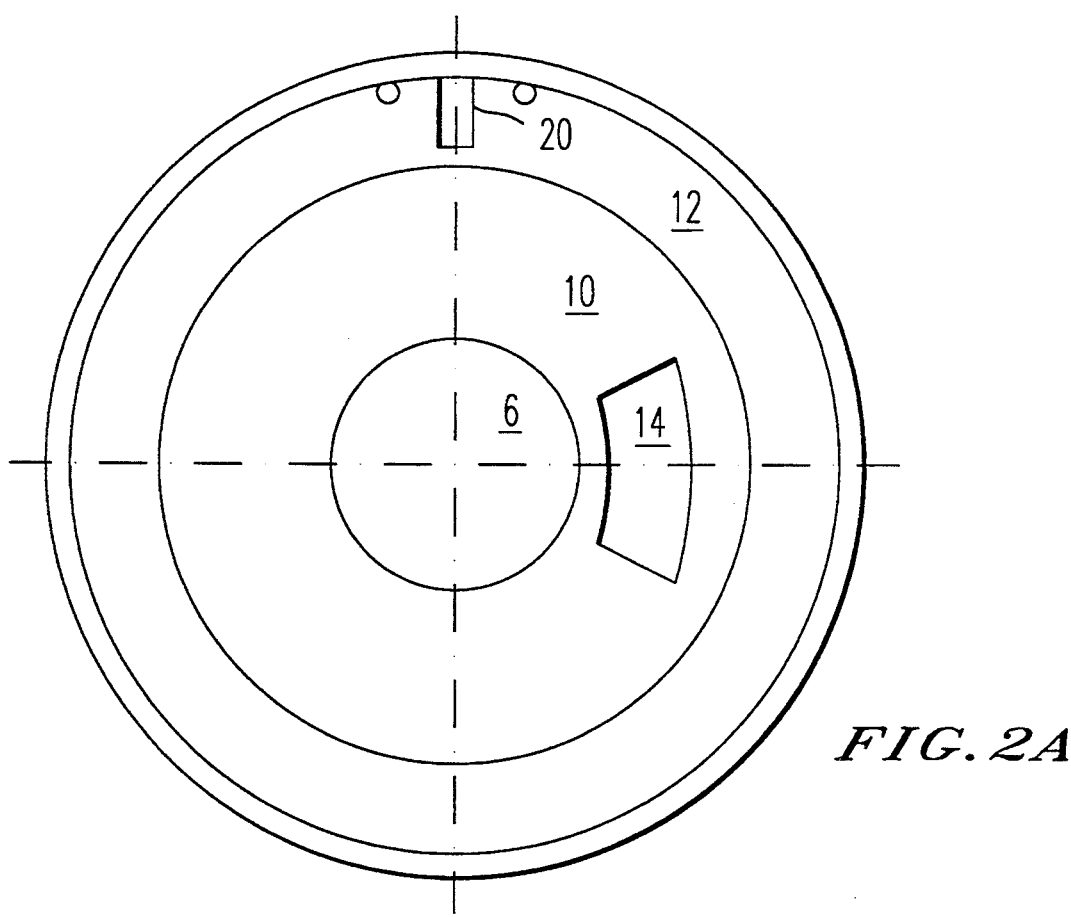
FIG. 2A shows a horizontal sectional view of the body of the inhaler.
Figure 2B:
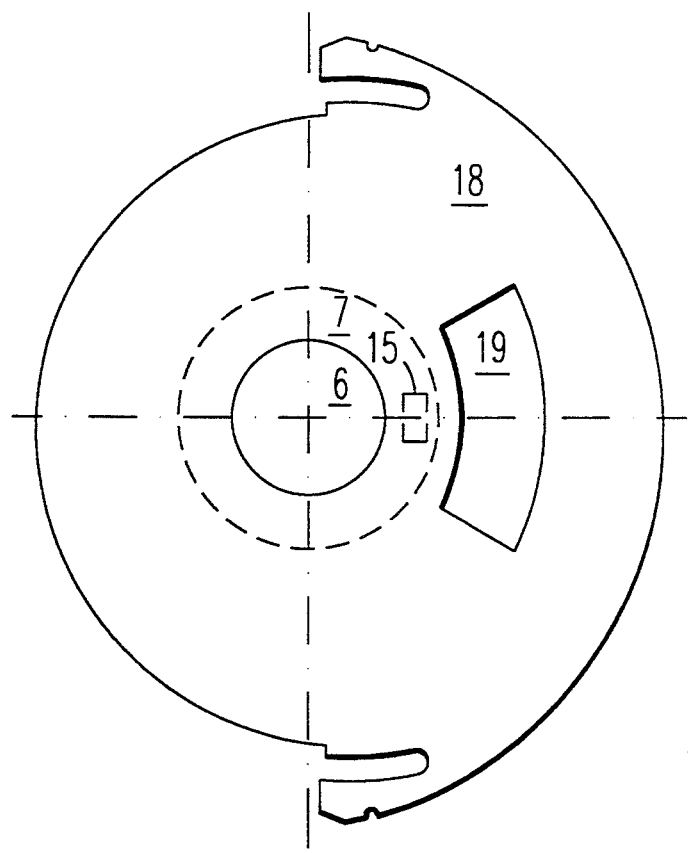
FIG. 2B shows a top view of the dispensing disk of the inhaler.

The positions of the holes 19 and 14 can be seen more clearly in FIG. 2A and 2B, respectively, showing a) at the top, a horizontal section of the body of the inhaler formed at the disc 10 and after removal of the diaphragm 17, and b) at the bottom, a top view of the dispensing disc 18. In the rest position, the holes 19 and 14 register with one another, but are separated by the diaphragm 17 which is itself provided with a hole of corresponding length situated in the opposite position with respect to the holes 14 and 19.

FIGS. 2A and 2B also show the teeth provided in the dispensing disc 18 and the projection 20 provided on the base of the body of the inhaler, engaging alternately the teeth, creating two closed positions, the first adapted for loading of the dose and the second adapted for dispensing of the dose into the chamber 24.

Upon inhalation, the air passes through the aspiration slots 23 into the chamber 24, in which the dose of powder delivered has been previously metered, therefore creating a negative pressure drawing an in flow of air from the outside into the interior of the chamber. The air flow is mixed with the powder, and the subsequent turbulence breaks up large aggregates of the powder into small particles, which by means of the central channel 6, are carried out as far as the cavity of the nozzle, from where they are directly inhaled.

As already stated hereinbefore, the dimensions of the circular channel 6, together with the provision of the slot means 23, are critical in order to obtain optimum flow characteristics and the disaggregation of the large aggregates.

In the preferred embodiment of the invention, this central conduit has a diameter of between 3 and 5 mm and a height of between 2.5 and 4 cm.

Disaggregation of the powder can be optionally further promoted by the presence in the cylindrical conduit 6 of helical blades 30 or a tapering zone 31.

Figure 3A:
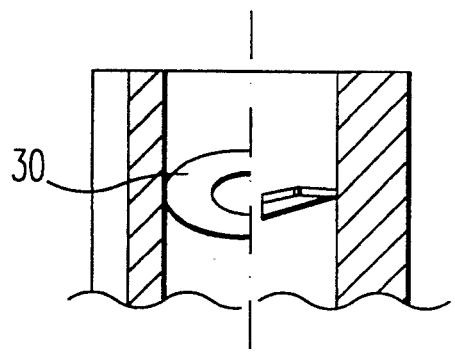
FIG. 3A shows a sectional view of the channel and helical blades of the inhaler.
Figure 3B:
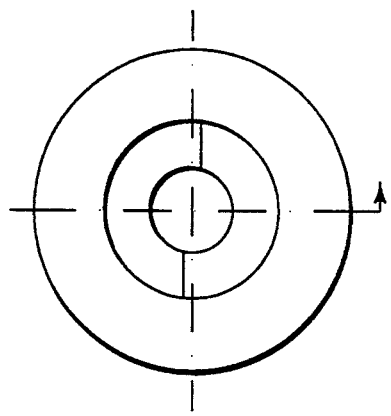
FIG. 3B shows a top view of FIG. 3A.
Figure 3C:
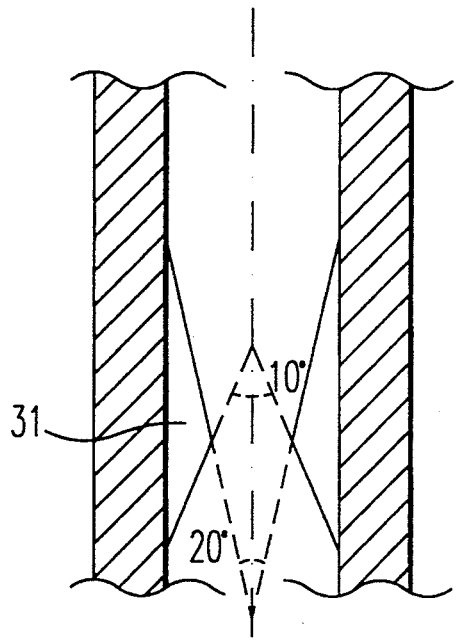
FIG. 3C shows a sectional view of the channel with a tapering zone.

Solutions of this type are illustrated in FIGS. 3A, 3B and 3C, showing respectively:

a) a longitudinal section and
b) a top view of the helical blades;
c) a longitudinal view of the circular tapering zone in the form of a Venturi tube, which, in a preferred embodiment of the invention, has an angle of 20° in the zone of convergence and an angle of 40° in the zone of divergence.

The advantages of the new inhaler, both with respect to the previous apparatus of the Applicant, forming the object of British Patent No. 2041763, and with respect to other inhalers de scribed subsequently in other patents or patent applications, will be clear from the description and from the drawings.

The most important feature is the improvement of the flow and the characteristics thereof, a number of factors contributing to this to a greater or lesser extent, such as;

optimization of the dimensions of the central channel, absolutely and in relation to the cavity of the nozzle;

enlarging the ventilation chamber which helps to reduce the flow resistance and to promote mixing of the air and the powder;

the air intake system formed by a series of slots 23 provided in the external body 21 which are connected together to form a circular space between the main body 2 and the external body 21.

This system of apertures has various technical advantages:

a) it promotes the inflow of air from the outside and directs it into the ventilation chamber through corresponding slots provided in the lower part of the rotating body;

b) accidental obstruction of the air flow as a result of incorrect positioning of the fingers on the part of the patient is rendered impossible;

c) it completely prevents spillage of powder from the container, even if the said container is turned upside down.

We calculated the flow characteristics of the inhaler in a preferred embodiment of the invention (A) in comparison with the inhaler of the British Patent No. 2041763 (B) by measuring the pressure drop in the apparatus.

Calculations were performed for flow rates of 20, 40, 60 l/min and the following total pressure drops were calculated:

| Flow rate l/min | Pressure drop (Pa) | |
| --- | --- | --- |
|  | A | B |
| 20 | 310 | 1670 |

-continued

| Flow rate l/min | Pressure drop (Pa) | |
| --- | --- | --- |
| | A | B |
| 40 | 1455 | 6600 |
| 60 | 4397 | 14800 |

The pressure drop was distributed as follows:

| | A | B |
| --- | --- | --- |
| Concentrical wall: | 24% | 66% |
| Bottom channel: | 31% | 15% |
| Cylindrical channel: | 45% | 3% |

From the calculations above it can be seen how a much better pressure drop distribution has been obtained.

Moreover it has been surprisingly noticed that small differences in the central channel, as for example the presence or the absence of a dot in the middle of the bottom, the presence of a restriction in the central channel and small differences in the height to the channel cause considerable differences of pressure drop, as it can be seen by comparing 3 different apparatus, indicated as C, D, E.

| Flow rate (l/s) | Pressure drop (Pa) |
| --- | --- |
| Pressure Drop inhaler type C | |
| (restrictor in the central channel; no dot in the bottom) | |
| 17 | 887 |
| 34 | 2982 |
| 54 | 8849 |
| Pressure Drop inhaler type D | |
| (no restrictor; no dot in the bottom) | |
| 17 | 392 |
| 34 | 1844 |
| 53 | 5228 |
| Pressure Drop inhaler type E | |
| (as C, but with the height of the bottom channel increased by 1 mm) | |
| 17 | 736 |
| 35 | 3551 |
| 55 | 10539 |

In addition to the particular flow characteristics, the inhaler of the invention offers other particularly useful technical solutions for the purposes of correct and reliable therapeutic use:

1. simplicity of operation;
2. uniformity of dosage, by virtue of the fact that it is possible to mix the active principle with a solid diluent, such as lactose, thereby increasing the weight of the single dose, particularly of very active compounds used in very small doses;
3. constancy and reproducibility of the dosage by virtue of the elimination of zones of friction as a result of the spillage capacity of powder: the powder in fact remains within well-defined zones and the distribution and dispensing system is such that it prevents occasional losses;
4. adaptability of the apparatus to different dosage schemes and to different types of drugs by virtue of the fact that it is possible to vary the volume of the chamber as a function of the quantity by weight of powder, between 25 and 30 mg. This adaptability means that it is possible to use powders having different characteristics with respect to granulometry and density;
5. reliability of the dosage by virtue of the delivery system, which comprises a first rotation through 180° in one direction for loading the powder into the dosing hole 14 and a second rotation through 180° in the opposite direction for dispensing the dose into the collecting chamber. This accuracy of movement prevents the accidental delivery of multiple doses.
6. Inviolability of the container as a result of the system of assembly, such that once the various components of the main body are inserted, the positioning of the closure element 9 seals together all of the parts of the body of the inhaler;
7. possibility of removing the nozzle in a simple manner in order to clean it and, moreover, replacing it in a simple manner.

We claim:

1. A powdered medicinal substance inhaler comprising:

a nozzle having an aperture for permitting the passage of a respirable powdered medicinal substance when a user inhales through said aperture;

a main body on which said nozzle is rotatably mounted, said main body comprising a circular storage chamber for storing said powdered medicinal substance and a base portion;

a ventilation chamber located below said base of said main body for receiving said powdered medicinal substance and air, said ventilation chamber comprising a powdered medicinal substance inlet for permitting a passage of said powdered medicinal substance from said circular storage chamber to said ventilation chamber;

a channel having an inlet end connected to said ventilation chamber and an outlet end connected to said nozzle for providing a passage for said powdered medicinal substance from said ventilation chamber to said nozzle;

first slot means leading into said ventilation chamber for permitting, when said user inhales through said aperture, a negative pressure to be created in said ventilation chamber so as to draw air into the ventilation chamber through said first slot means, said drawn in air mixing with the powdered medicinal substance in said ventilation chamber for breaking up large aggregates of said powdered medicinal substance into small particles and conveying said powdered medicinal substance comprised of said small particles through said channel and to the user by way of said nozzle and aperture; and an external body located below said main body and having an upper portion which overlaps and circumferentially surrounds said base of the main body in a spaced manner for forming a circular space between the base of the main body and the upper portion of the external body, said first slot means being defined by said circular space and extending between the base of the main body and the upper portion of the external body, said external body comprising a lower portion which defines a lower chamber and second slot means extending between said lower chamber and said circular storage chamber, said lower chamber containing a dehumidifying means for absorbing moisture in the powder in the circular storage chamber;

wherein:

a size of said ventilation chamber and a length and diameter of said channel permit a localized resistance to flow of air at the inlet end of the channel where mixing of air and powder occurs, said channel having a length in a range of 2.5 to 4 cm and a diameter in a range of 3 to 5 mm.

2. An inhaler according to claim 1, wherein said channel has a circular cross-section.

3. The inhaler according to claim 1, wherein said storage chamber of said main body is of sufficient volume for storing an amount of medicinal substance required for a predetermined treatment cycle, and said inhaler comprises measuring means for delivering successive measured doses of said medicinal substance to said ventilation chamber.

4. The inhaler according to claim 3, wherein said main body comprises a dosing hole and said measuring means includes a rotary assembly having stop means to prevent rotation of the assembly past a first position when rotated in a first direction and stop means to prevent rotation of said assembly past a second position when rotated in a second direction, said rotary assembly having a rotating dosing diaphragm with an admitting opening which connects with said storage chamber and registers with a first end of the dosing hole in said main body to admit a measured amount of the medicinal substance into said dosing hole during a portion of the rotation of the assembly in one of said directions, said assembly also having a dispensing disc which closes off a second end of said dosing hole while said admitting opening and dosing hole first end are in registry, said dispensing disc also having a dispensing opening which connects with said ventilation chamber and registers with said second end of said dosing hole to discharge said measured portion into said ventilation chamber during a portion of the rotation of the assembly in an opposite direction to said one direction.

* * * * *